United States Patent [19]

Yamazaki et al.

[11] Patent Number: 4,607,116

[45] Date of Patent: Aug. 19, 1986

[54] PROCESS FOR PREPARING DIARYLS

[75] Inventors: Yasuo Yamazaki, Machida; Takehiko Suzuki; Masaharu Uchiyama, both of Tokyo, all of Japan

[73] Assignee: Nippon Petrochemicals Company Limited, Tokyo, Japan

[21] Appl. No.: 587,376

[22] Filed: Mar. 8, 1984

[30] Foreign Application Priority Data

Mar. 9, 1983 [JP] Japan .................................. 58-37313

[51] Int. Cl.$^4$ .................... C07C 67/30; C07C 51/347; C07C 41/24; C07C 76/02; C07C 102/00; C07C 17/24; C07C 1/26
[52] U.S. Cl. .................. 560/21; 260/350 R; 570/190; 570/191; 502/117; 585/422; 585/427; 502/155; 585/457; 560/56; 560/61; 560/62; 560/64; 560/65; 560/80; 560/81; 560/83; 560/96; 560/100; 560/102; 562/435; 562/466; 562/467; 562/469; 562/488; 562/490; 562/492; 564/155; 564/168; 564/192; 568/592; 568/642; 568/643; 568/928; 568/931; 570/129; 570/130; 570/144
[58] Field of Search .................. 585/422, 427, 457; 564/155, 168, 192; 568/592, 642, 643, 928, 931; 570/129, 130, 144, 190, 191; 560/80, 81, 83, 56, 61, 62, 64, 65, 96, 21, 100, 102; 562/435, 466, 467, 488, 490, 492, 469; 502/117, 155

[56] References Cited

U.S. PATENT DOCUMENTS 4,542,233  9/1985  Piccolo et al. ....................... 560/21

Primary Examiner—Natalie Trousof
Assistant Examiner—Vera C. Clarke
Attorney, Agent, or Firm—Scully, Scott, Murphy & Presser

[57] ABSTRACT

Provided is a process for preparing a diaryl or a mixture of diaryls represented by any or a combination of the following formulae (II), (III) and (V), characterized in that a diaryliodonium salt represented by the following formula (I) is reacted in a solvent in the presence of a transition metal catalyst and a reducing metal at a temperature in the range of room temperature to 100° C.:

$$[Ar_1\text{-}I^{\oplus}\text{-}Ar_2]X^{\ominus} \quad \text{(I)}$$

$$Ar_1\text{-}Ar_1 \quad \text{(II)}$$

$$Ar_1\text{-}Ar_2 \quad \text{(III)}$$

$$Ar_2\text{-}Ar_2 \quad \text{(IV)}$$

wherein $Ar_1$ and $Ar_2$, which may be alike or different, are each an aryl group which may have a substituent group or groups and $X^{\ominus}$ is a counter ion which is inert to said reaction.

6 Claims, No Drawings

PROCESS FOR PREPARING DIARYLS

BACKGROUND OF THE INVENTION

The present invention relates to a novel process for preparing diaryls from diaryliodonium salts.

Heretofore, as methods for preparing diaryls, e.g. biphenyl, there have been reported a method in which iodobenzene and copper are reacted, a method in which benzene is dimerized by passing through a heated iron tube, and a method which employs an alkali metal such as sodium and bromobenzene.

OBJECT OF THE INVENTION

The object of the present invention is to provide a novel process for preparing diaryls.

SUMMARY OF THE INVENTION

The present invention is concerned with a process for preparing a diaryl or a mixture of diaryls presented by any or a combination of the following formulae (II), (III) and (IV), characterized in that a diaryliodonium salt represented by the following formula (I) is reacted in a solvent in the presence of a transition metal catalyst and a reducing metal at a temperature in the range of room temperature to 100° C.:

$$[Ar_1\text{-}I^\oplus\text{-}Ar_2]X^\ominus \quad (I)$$

$$Ar_1\text{-}Ar_1 \quad (II)$$

$$Ar_1\text{-}Ar_2 \quad (III)$$

$$Ar_2\text{-}Ar_2 \quad (IV)$$

wherein $Ar_1$ and $Ar_2$, which may be alike or different, are each an aryl group which may have a substituent group or groups and $X^\ominus$ is a counter ion which is inert to the above reaction.

DETAILED DESCRIPTION OF THE INVENTION

In the present invention, diaryliodonium salts of the foregoing formula (I) are used as starting materials. Each aryl group is a monovalent substituent group derived by removing one hydrogen atom from the aromatic nucleus of a condensed or non-condensed type aromatic hydrocarbon which may have any substituent groups. For example, it is derived from a non-condensed type aromatic hydrocarbon such as benzene or indane, or a condensed type aromatic hydrocarbon such as naphthalene. The two aryl groups may be the same or different. On the aromatic nucleus there may be present one or more substituent groups, which may be either electron attractive or donative or both electron attractive and donative. Examples of such substituents are $C_1$-$C_{12}$ alkyl or cycloalkyl, aryl, halogenoalkyl, halogen, carboxyl, alkoxy, alkoxycarbonyl, alkoxycarbonylalkyl, nitro and N-acylamino.

Preferred diaryliodonium salts are such diphenyliodonium salts as represented by the following formula:

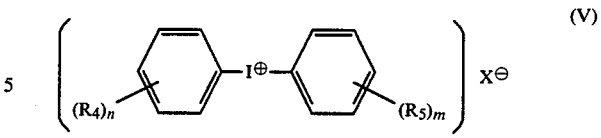

wherein n or m is an integer of 0 to 3, and each $R_4$ or $R_5$, which may be the same or different, is selected from hydrogen atom, $C_1$-$C_{12}$ alkyl or cycloalkyl groups, aryl groups, halogenoalkyl groups, halogen atom, carboxyl group, alkoxy groups, alkoxycarbonyl groups, alkoxycarbonylalkyl groups, nitro and N-acylamino groups.

Examples of aryl as $R_4$ or $R_5$ are phenyl, tolyl and naphthyl. Examples of halogenoalkyl are chloromethyl and bromomethyl. Examples of alkoxy are methoxy, ethoxy and propoxy. Examples of alkoxycarbonyl are methoxycarbonyl and ethoxycarbonyl, and examples of alkoxycarbonylalkyl are methoxycarbonylmethyl and ethoxycarbonylethyl. Examples of N-acylamino are N-acetylamino, N,N-diacetylamino and succinimido.

As examples of symmetric type diaryliodonium ion wherein the two aryl groups are the same, mention may be made of diphenyliodonium, ditolyliodonium, dicumenyliodonium, bis(alkylphenyl)iodoniums such as bis(iso-butylphenyl)iodonium and bis(t-butylphenyl)iodonium, bis(cyclohexylphenyl)iodonium, dibiphenylyliodonium, bis(halogenoalkylphenyl)iodoniums such as bis(trifluoromethylphenyl)iodonium, bis(halogenophenyl)iodoniums such as bis(chlorophenyl)iodonium and bis(bromophenyl)iodonium, bis(carboxylphenyl)iodonium, bis(alkoxyphenyl)iodoniums such as bis(methoxyphenyl)iodonium and bis(ethoxyphenyl)iodonium, bis(nitrophenyl)iodonium, and bis(acylaminophenyl)iodoniums such as bis(acetylaminophenyl)iodonium.

There also may be used asymmetric type diaryliodonium salts wherein the two aryl groups are different, examples of which are salts of 4-tolylphenyliodonium, 4-t-butylphenylphenyliodonium, 4-methoxyphenylphenyliodonium, 3-chlorophenylphenyliodonium, 4-bromophenylphenyliodonium and 4-chlorophenyl-4'-methylphenyliodonium.

These diaryliodoniums form salts with the counter ion $X^\ominus$ as shown in the foregoing formulae (I) and (V), but the counter ion $X^\ominus$ is not essential to the present invention; it may be any anion inert to the reaction. Examples of counter ions, which usually are selected according to methods of obtaining iodonium salts, include mineral acid anions such as bisulfate ion, chloride ion, bromide ion and iodide ion, and metal halide ions such as boron tetrafluoride ion, phosphorus hexafluoride ion, arsenic hexafluoride ion and antimony hexafluoride ion. These counter ions may be ion-exchanged with each other. Bromide and other halide ions are particularly preferred.

Halogen salts of diaryliodoniums can be produced according to the method described in British Pat. Nos. 1,114,950; 1,542,068; and 1,572,620, or the Beringer et al's method described in J. Am. Chem. Soc. 81, 342 (1959), for example, can be produced from alkylbenzenes such as benzene, toluene, iso-propylbenzene, iso-butylbenzene and t-butylbenzene, indane, halogenated benzenes such as chlorobenzene and bromobenzene, benzoic acid, anisole, nitrobenzene, acetanilide, and biphenyl. As an example, in the method of producing diphenyliodonium salt from benzene, benzene and potassium iodate (KIO₃) are added into acetic anhydride and mixed, then a mixed solution of acetic anhydride and concentrated sulfuric acid is dropwise added and stirred, thereafter an aqueous saturated ammonium chloride solution is added to allow precipitation to take place, followed by filtration and recrystallization, whereby the diphenyliodonium chloride can be obtained, which may be further subjected to ion exchange, if required.

By reacting the diaryliodonium salts exemplified above in a solvent in the presence of a transition metal catalyst and a reducing metal, there can be obtained diaryls of the foregoing formulae (II)–(IV). This can be expressed by the following reaction formula:

$$2[Ar\text{-}I^{\oplus}\text{-}Ar] \rightarrow Ar\text{-}Ar + 2ArI$$

The aryl groups of the resultant diaryls are any of the aryl groups of the starting diaryliodonium salts. Therefore, from the diaryliodonium salts of the formula (I) there are obtained the following three kinds of combinations of diaryls:

$$Ar_1\text{-}Ar_1 \quad\quad (II)$$

$$Ar_1\text{-}Ar_2 \quad\quad (III)$$

$$Ar_2\text{-}Ar_2 \quad\quad (IV)$$

More specifically, from a symmetric type iodonium salt where the two aryl groups are the same there is obtained only one kind of diaryl, for example, biphenyl from diphenyliodonium salt, 4,4'-dimethylbiphenyl from 4,4'-ditolyliodonium salt, and 4,4'-dichlorobiphenyl from bis(4-chlorophenyl)iodonium salt. On the other hand, from an asymmetric diaryliodonium salt wherein the two aryl groups are different there is obtained a mixture of diaryls of the above formulae (II)–(IV), for example, a mixture of biphenyl, 4-methylbiphenyl and 4,4'-dimethylbiphenyl is obtained from 4-tolylphenyliodonium salt.

The transition metal catalyst used in the present invention comprises a metal selected from Group VIII in the Periodic Table, for example, palladium, rhodium, ruthenium, platinum, iridium, osmium, or nickel, with a palladium catalyst being particularly preferred. These transition metals may be used as catalysts in various forms regardless of their oxidation numbers or whether they are in the form of complexes or not. In the case of palladium, for example, there may be used palladium black, palladium supported on alumina or active carbon, divalent palladium compounds such as palladium halides, e.g. palladium chloride, palladium oxides and palladium salts of lower fatty acids, e.g. palladium acetate, as well as complexes such as bis(dibenzylideneacetone)palladium, acetylacetonepalladium, tetrakis(triphenylphosphine)palladium, bis(triphenylphosphine)dichloropalladium, and bis(triphenylphosphine)phenylpalladium iodide. In the case of rhodium, there also may be used its carbonyl complex. Examples of nickel catalysts include nickel (II) chloride and bis(triphenylphosphine)nickel (II) chloride.

The amount of the transition metal catalyst used is in the range of 0.1 to 10 mol%, preferably 1 to 5 mol%, per mol of the iodonium salt.

As the reducing metal used together with the transition metal, there may be used any metal if only it can reduce the transition metal as catalyst under the reaction condition of the present invention. For example, there may be used the metals of Group IIB in the Periodic Table and other metals, such as zinc, copper, tin, mercury, silver, etc., each alone or in combination. Even alloys may be used. Particularly, metallic zinc is preferable in that it affords a high yield. The reducing metal is used in an amount sufficient to neutralize the counter ion of the diaryliodonium salt to be reacted.

As the solvent used in the invention, there may be used any inert solvent which dissolves the diaryliodonium salt even a little and which does not participate in the reaction. Examples are lower alcohols such as methanol and ethanol, ketones such as acetone and methyl ethyl ketone, ethers such as dimethoxyethane, tetrahydrofuran and dioxane, as well as various polar solvents such as dimethylformamide (DMF), dimethyl sulfoxide (DMSO) and acetonitrile.

The reaction proceeds gently and quickly, and the reaction pressure and temperature may be selected according to the starting material used. Usually, atmospheric pressure suffices as the reaction pressure, it being not necessary to specially apply pressure, provided that pressure may be applied to prevent the evaporation of the solvent. The reaction temperature may be in the range from room temperature to 100° C. Preferably, it is below the boiling point of the solvent used. Further, a reaction time not longer than one hour usually suffices.

If the reaction after completion is followed by a thorough washing with water, extraction with ether for isolation and subsequent distillation or recrystallization, there can be obtained the diaryl or diaryls as the object product of the present invention.

In the reaction there is by-produced an iodoaryl, e.g. iodobenzene, as shown in the foregoing reaction formula. Since iodine is expensive and hence iodobenzene is also expensive, the utilization of the by-produced iodoaryl must be considered in order to render the process of the present invention economical and less expensive. As one method for utilizing the by-produced iodoaryl, there may be obtained a diaryliodonium salt from the by-produced iodoaryl, for example, according to the foregoing Beringer et al's method or the method disclosed in the specification of Japanese Patent Application No. 3731/1983 which was filed by the present applicant. Thus, if a diaryliodonium salt is obtained from the by-produced iodoaryl, the expensive iodine, that is, the iodoaryl, is utilized in a recycled manner without being lost, and consequently the process of the present invention becomes more economical.

In the present invention, the by-produced iodoaryl mentioned above further undergoes another reaction under some particular reaction conditions, resulting in that iodine is converted to a neutral iodine salt. In the form of such a neutral salt, the re-utilization of iodine is difficult. Therefore, it is necessary that the process of the present invention be practised under conditions under which the by-produced iodobenzene will not undergo a further reaction. This requirement is satisfied if the reducing metal is not used in an excess amount or if the reaction is carried out at a relatively low temperature, more specifically, if the reducible metal is used in an amount of 0.4 to 0.6 mol per mol of the diaryliodonium salt or if the reaction is carried out at a temperature in the range from room temperature to 80° C.

The following examples are given to further illustrate the present invention.

EXAMPLE 1

THF (50 ml), various diaryliodonium salts (20 mmol each) set forth in Table 1, metallic zinc (20 mg-atom) and catalysts (1 mmol each) were charged into flasks and stirred at room temperature for 30 minutes. Then, the catalysts were filtered off, followed by distillation to isolate products. The products were analyzed by gas chromatography and identified by IR spectra, NMR spectra and melting points, the results of which are as set out in Table 1. There were by-produced iodobenzene, p-methyliodobenzene and p-chloroiodobenzene quantitatively in Run Nos. 1–8, No. 9 and No. 10, respectively.

TABLE 1

| Run No. | Diaryl-iodonium Salt[1] | Catalyst[2] | Counter Ion | Diaryl | Yield |
|---|---|---|---|---|---|
| 1 | A | Pd(OAc)$_2$ | Cl$^\ominus$ | biphenyl | 62 |
| 2 | A | Pd(acac)$_2$ | " | " | 96 |
| 3 | A | PdCl$_2$ | " | " | 28 |
| 4 | A | Pd(p$\phi_3$)$_2$Cl$_2$ | " | " | 33 |
| 5 | A | Pd(dba)$_2$ | " | " | 36 |
| 6 | A | Pd(acac)$_2$ | Br$^\ominus$ | " | 94 |
| 7 | A | " | I$^\ominus$ | " | 50 |
| 8 | A | " | BF$_4^\ominus$ | " | 53 |
| 9 | B | " | Br$^\ominus$ | 4,4'-dimethyl-biphenyl | 82 |
| 10 | C | " | " | 4,4'-dichloro-biphenyl | 76 |
| 11[3] | A | Pd(acac)$_2$ | Cl$^\ominus$ | dichloro-biphenyl | 29 |

[1] A: diphenyliodonium salt, B: 4,4'-ditolyliodonium salt, C: bis(4-chlorophenyl)iodonium salt
[2] acac: acetylacetone, dba: dibenzylideneacetone, p$\phi_3$: triphenylphosphine
[3] Metallic copper was used in place of metal zinc.

EXAMPLE 2

Using symmetric type diaryliodonium salts having various substituent groups, reaction was carried out in the same way as in Example 1, the results of which are as set out in Table 2. The melting points of those iodonium salts are shown below. Also as to asymmetric type diaryliodonium bromides, reaction was conducted in the same manner, the results of which are as shown in Table 3. In both cases, Pd(acac)$_2$ was used as catalyst.

| Diaryliodonium salts | Melting points |
|---|---|
| bis(4-hepthylphenyl) iodonium bromide | past like |
| bis(4-cyclohexylphenyl) iodonium bromide | 175° C. |
| bis(4-methoxyphenyl) iodonium bromide | 201–202° C. |
| bis(3-carboxyphenyl) iodonium iodide | 154–156° C. |
| bis(4-methoxycarbonylphenyl) iodonium chloride | 239–241° C. |
| bis-4-(methoxycarbonylmethyl) phenyl iodonium bromide | 166–167° C. |
| bis(4-succinimidophenyl) iodonium iodide | 184–185° C. |
| bis(3-nitrophenyl) iodonium bromide | 174–176° C. |

TABLE 2

| Run No. | Diaryliodonium salts | Diaryl | Yield (%) |
|---|---|---|---|
| 12 | bis(4-heptylphenyl)iodonium bromide | 4,4'-diheptylbiphenyl | 93 |
| 13 | bis(4-cyclohexylphenyl)iodonium bromide | 4,4'-dicyclohexylbiphenyl | 92 |
| 14 | 4,4'-biphenyliodonium | p-quaterphenyl | 90 |
| 15 | bis(chloromethylphenyl)iodonium | 4,4'-di(chloromethyl)-biphenyl | 75 |
| 16 | bis(4-methoxyphenyl)iodonium bromide | 4,4'-dimethoxybiphenyl | 82 |
| 17 | bis(3-carboxyphenyl)iodonium iodide | 3,3'-dicarboxybiphenyl | 65 |
| 18 | bis(4-methoxycarbonylphenyl)iodonium chloride | 4,4'-di(methoxycarbonyl)-biphenyl | 81 |
| 19 | bis(4-carboxymethylphenyl)iodonium bromide | 4,4'-di(carboxymethyl)-biphenyl | 81 |
| 20 | bis [4-(methoxycarbonylmethyl)phenyl]iodonium bromide | 4,4'-di(methoxycarbonyl-methyl)biphenyl | 82 |
| 21 | bis(4-succinimidophenyl)iodonium iodide | 4,4'-disuccinimidobiphenyl | 85 |
| 22 | bis(3-nitrophenyl)iodonium bromide | 3,3'-dinitrobiphenyl | 91 |

TABLE 3

| Run No. | Diaryliodonium Bromide Iodonium | m.p. | Diaryl | | Yield (%) |
|---|---|---|---|---|---|
| 23 | 4-tolylphenyliodonium | 175–176 | biphenyl<br>4-methylbiphenyl<br>4,4'-dimethylbiphenyl | (28%)<br>(51%)<br>(21%) | 95 |
| 24 | 4-chlorophenylphenyliodonium | 167–168 | biphenyl<br>4-chlorobiphenyl<br>4,4'-dichlorobiphenyl | (17%)<br>(52%)<br>(30%) | 90 |
| 25 | 4-methoxyphenylphenyliodonium | 184–185 | biphenyl<br>4-methoxybiphenyl<br>4,4'-dimethoxybiphenyl | (30%)<br>(51%)<br>(19%) | 91 |
| 26 | 4-t-butylphenylphenyliodonium | 198–200 | biphenyl<br>4-t-butylbiphenyl<br>4,4'-di-t-butylbiphenyl | (28%)<br>(53%)<br>(19%) | 94 |
| 27 | 4-chlorophenyl-4-tolyliodonium | 192–193 | 4-methyl-4'-chlorobiphenyl<br>4,4'-dichlorobiphenyl<br>4,4'-dimethylbiphenyl | (50%)<br>(28%)<br>(22%) | 95 |

What is claimed is:

1. A process for preparing a diaryl or a mixture of diaryls represented by at least one of the following formulae (II), (III) and (IV), characterized in that a diaryliodonium salt represented by the following formula (I) is reacted in a solvent in the presence of a transition metal catalyst and a reducing metal at a temperature in the range of room temperature to 100° C.:

$$[Ar_1\text{-}I^{\oplus}\text{-}Ar_2]X^{\ominus} \quad (I)$$

$$Ar_1\text{-}Ar_1 \quad (II)$$

$$Ar_1\text{-}Ar_2 \quad (III)$$

$$Ar_2\text{-}Ar_2 \quad (IV)$$

wherein $Ar_1$ and $Ar_2$, which may be alike or different, are each an aryl group which may be unsubstituted or substituted with at least one group which is $C_1$–$C_{12}$ alkyl, cycloalkyl groups, aryl groups, halogenoalkyl groups, halogen, carboxyl, alkoxy groups, alkoxylcarbonyl groups, alkoxycarbonylalkyl groups, nitro, and N-acylamino groups; and $X^{\ominus}$ is a counter ion which is inert to said reaction.

2. The process of claim 1, wherein said aryl group $Ar_1$ or $Ar_2$ is represented by the following formula:

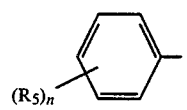

wherein n is an integer of 0 to 3, and each $R_5$, which may be the same or different, is selected from the group consisting essentially of hydrogen, $C_1$–$C_{12}$ alkyl and cycloalkyl groups, aryl groups, halogenoalkyl groups, halogen carboxyl, alkoxy groups, alkoxycarbonyl groups, alkoxycarbonylalkyl groups, nitro, and N-acylamino groups.

3. The process of claim 1, wherein said transition metal catalyst is a palladium-based catalyst.

4. The process of claim 1, wherein said reducing metal is metallic zinc, metallic copper, tin, mercury, silver or alloys thereof.

5. The process of claim 1, wherein the reducing metal is used in an amount of 0.4 to 0.6 mol per mol of the diaryliodonium salt.

6. The process of claim 1, wherein the reaction is carried out at a temperature in the range from room temperature to 80° C.

* * * * *

UNITED STATES PATENT AND TRADEMARK OFFICE
CERTIFICATE OF CORRECTION

PATENT NO. : 4,607,116

DATED : August 19, 1986

INVENTOR(S) : Yasuo Yamazaki, et al.

It is certified that error appears in the above-identified patent and that said Letters Patent is hereby corrected as shown below:

In Abstract, line 3: change --(V)-- to --(IV)--

Signed and Sealed this

Eighteenth Day of August, 1987

Attest:

DONALD J. QUIGG

*Attesting Officer*    *Commissioner of Patents and Trademarks*